United States Patent [19]

Signorino et al.

[11] Patent Number: 5,595,592

[45] Date of Patent: Jan. 21, 1997

[54] DYE COMPOSITIONS AND METHODS FOR FILM COATING TABLETS AND THE LIKE

[75] Inventors: Charles A. Signorino, Norristown, Pa.; Harry Meggos, Alton, Ill.

[73] Assignee: Warner-Jenkinson Company, Inc., St. Louis, Mo.

[21] Appl. No.: 345,930

[22] Filed: Nov. 28, 1994

Related U.S. Application Data

[62] Division of Ser. No. 21,785, Feb. 24, 1993, Pat. No. 5,411,746.

[51] Int. Cl.$^6$ .................. C09D 1/00; C09D 101/28; C09D 103/02; C09D 105/00

[52] U.S. Cl. ................. 106/198.1; 106/20 R; 106/26 R; 106/25 A; 106/185.1; 106/186.1; 106/205.6; 106/205.71; 106/205.9; 106/214.2; 106/215.4; 106/419; 106/430; 106/436; 106/439; 106/442; 106/459; 523/202; 424/475; 424/480

[58] Field of Search ............... 106/163.1, 20 R, 106/25 A, 260 R, 185.1, 186.1, 205.6, 205.71, 205.9, 214.2, 215.4, 419, 430, 436, 439, 442, 459, 198.1; 523/202; 424/475, 480; 427/3

[56] References Cited

U.S. PATENT DOCUMENTS

| | | | |
|---|---|---|---|
| 4,340,582 | 7/1982 | Kriesel et al. | 424/480 |
| 4,543,370 | 9/1985 | Porter et al. | 523/100 |
| 4,661,367 | 4/1987 | Forse et al. | 427/3 |
| 4,802,924 | 2/1989 | Woznicki et al. | 424/480 |
| 4,880,636 | 11/1989 | Franz | 424/480 |
| 4,931,286 | 6/1990 | Johnson et al. | 424/480 |
| 5,037,797 | 8/1991 | Kumamoto et al. | 503/214 |
| 5,248,516 | 9/1993 | Wheatley et al. | 427/214 |

OTHER PUBLICATIONS

Remington's Pharmaceutical Sciences, 8th Edition, (1990), Mack Publishing Co., Easton, PA, pp. 1671, 1668–1669.

*Primary Examiner*—David Brunsman
*Attorney, Agent, or Firm*—Whyte Hirschboeck Dudek S.C.

[57] ABSTRACT

An improved dye composition for use in coating tablets and the like is constituted by a stable, aqueous suspension containing a water-soluble, nontoxic dye, an opacifying agent which may be titanium dioxide or iron oxide an immobilizing agent for immobilizing the dye and preventing it from migrating when applied to a tablet or the like, the immobilizing agent being constituted by a nontoxic metal salt present in an amount of from approximately 0.1 to 10 equivalents of metal per mole of dye, and water. The suspension may also contain a film-forming, water-soluble or water-dispersible edible polymer and a plasticizer. These compositions are used in lieu of lake compositions to produce tablets and the like with uniform, non-mottled coatings.

12 Claims, No Drawings

DYE COMPOSITIONS AND METHODS FOR FILM COATING TABLETS AND THE LIKE

This is a division of application Ser. No. 08/021,785, filed Feb. 24, 1993, now U.S. Pat. No. 5,411,746.

BACKGROUND OF THE INVENTION

This invention relates to dye compositions and, more particularly, to stable, aqueous dye suspensions for use in film coating tablets and the like to produce smooth, uniform, substantially non-mottled coatings.

Heretofore, it has been the practice to utilize FD&C lakes rather than water-soluble dyes as the materials of choice for coating tablets and the like. The problems attending coating tablets with water-soluble dyes has been noted in various patents and publications. For example, in an article entitled "Characterization Techniques for the Aqueous Film Coating Process" by Mathur et al., Pharmaceutical Technology, October 1984, it is noted that when water-soluble dyes are used in aqueous film coating, problems with color migration or mottling upon drying are encountered.

The dynamics of coating include the spreading of a thin wet layer of a coating suspension on a tablet which is dried rapidly after spreading. The drying dynamics usually lead to uneven distribution of a water-soluble dye in the dried layer. Though the color can be uniformly distributed in the coating suspension and applied very uniformly on the tablet, a mottled appearance normally results when water-soluble dyes are used. This is believed to be due to the dye molecules migrating in the film, being transported by the aqueous medium as it moves in the film layer surface and evaporates at distinct points. The dye thus accumulates at these points producing dark patches or mottling.

The use of lakes has overcome these problems because they are insoluble pigments which are manufactured by attaching dye molecules to aluminum hydroxide particles thereby rendering them water-soluble. These pigment particles or lakes are then dispersed in a coating suspension and applied uniformly to the surface of a table to produce a uniformly colored product because the pigment particles or lakes do not migrate in an aqueous medium.

Prior to 1960, it was the practice to sugar coat tablets and candies with water-soluble dyes dissolved in sugar syrup. However, since the development of lakes in 1959, most sugar coating is carried out with lakes. Film coating of tablets and the like with water-soluble dyes has never been successfully achieved due to the difficulty of obtaining uniform coating because of migration of the dyes in an aqueous medium.

It has also been known to utilize mixtures of lakes and water-soluble dyes in coating suspensions with the dyes being incorporated to reduce the coat and to obtain brighter color shades.

Because water-soluble dyes are less costly than lakes, it would be advantageous if such dyes could be used in coating suspensions in lieu of lakes while yet providing uniform, non-mottled coatings.

SUMMARY OF THE INVENTION

Among the objects of the present invention may be noted the provision of stable, aqueous suspension compositions which contain water-soluble dyes as the color component for coating tablets and the like; the provision of such compositions which further contain metal salt immobilizing agents to prevent the water-soluble dyes from migrating when applied to tablets and the like; the provision of such compositions which are economically advantageous in requiring less color to be utilized in achieving the same color effect; the provisions of compositions of this type which permit the production of coatings for tablets and the like which are smooth uniform and non-mottled and have more gloss and less brittleness than coatings produced with lakes; and the provision of methods of producing such smooth, uniform and non-mottled coatings on tablets and the like. Other objects and features will be in part apparent and in part pointed out hereinafter.

Briefly, the present invention is directed to a stable, aqueous suspension for use in preparing a coating composition for coating tablets and the like which comprises a water-soluble dye, an opacifying agent which may be titanium dioxide or iron oxide, a nontoxic immobilizing agent for immobilizing the dye and preventing it from migrating when applied to a tablet or the like, the nontoxic immobilizing agent being constituted by a nontoxic metal salt present in an amount of from approximately 0.1 to approximately 10 equivalents of metal per mole of dye, and water. Optionally, the composition may also contain a fluidizing agent. The invention is further directed to the above-noted suspension composition additionally containing a film-forming, water-soluble or water-dispersible, edible polymer such as hydroxypropylmethyl cellulose.

The invention, in another embodiment, is directed to a stable, aqueous suspension composition for use in preparing a coating composition for coating tablets and the like which comprises a water-soluble, nontoxic dye, an FD&C or D&C lake, the proportion by weight of lake to dye being in the range of approximately 1:1 to approximately 1:10, an opacifying agent, a fluidizing agent such as ethylene diamine tetraacetic acid, and water.

In still another embodiment, the invention is directed to a stable, dry concentrate for use in preparing an aqueous suspension which has the same composition set out above for the aqueous suspension but contains no water. The dry concentrate may also contain a fluidizing agent, a film-forming, water-soluble or water-dispersible edible polymer and a plasticizer.

In yet another embodiment, the invention is directed to the method of producing a smooth, uniform, substantially non-mottled coating on tablets and the like by preparing the above-described aqueous suspension composition containing a nontoxic immobilizing metal salt, mixing the suspension with an aqueous solution of a film-forming, water-soluble or water-dispersible, edible polymer to form a coating suspension, and then applying the coating suspension onto tablets or the like whereby the nontoxic immobilizing agent immobilizes the water-soluble dye and substantially prevents it from migrating, thereby producing a smooth, uniform, substantially non-mottled coating on the tablets or the like.

DESCRIPTION OF THE PREFERRED EMBODIMENTS

In accordance with the present invention, it has now been found that nontoxic, water-soluble dyes may be advantageously employed in lieu of lakes in the coating of tablets, candy pieces, nuts, seeds, capsules or granules by incorporating in the coating composition with such a dye an immobilizing agent which renders the dye insoluble or less mobile and substantially prevents it from migrating in the coating layer after application to a tablet or the like. This consequent immobilization of the dye, unexpectedly achieved through the present invention, prevents the classic mottling phenomenon encountered in the past when the use of water-soluble dyes produced unacceptable, uneven and mottled color in the coating of tablets and the like.

The immobilizing agent in accordance with the invention is a nontoxic metal salt which is present in the coating suspension in an amount from approximately 0.1 to approximately 10 equivalents of metal per mole of the water-soluble dye. More optimally, the best results are achieved when the ratio is approximately 0.5 to approximately 5 equivalents of metal per mole of dye, and more preferably 1 equivalent of metal per mole of dye. Any nontoxic metal salt may be employed and illustrative metal salts include alkaline earth metal salts, iron salts, aluminum salts and zinc salts. Among the preferred alkaline earth metals are calcium and magnesium, and such metals may be employed in the present invention in the form of chloride, acetate, nitrate, oxide, hydroxide, carbonate, sulfate, phosphate, silicate or other salts. The metal salt used may be either water-soluble or water-soluble, but it must be substantially nontoxic. A source of metal salt, such as talc or clay, may also be employed with the proportion of equivalents of metal per mole of the water-soluble dye being in the ranges described above.

The invention may be practiced to achieve the production of smooth, uniform, substantially non-mottled coatings with any nontoxic, water-soluble dye or mixture of two or more such dyes. The nontoxic, water-soluble dye may be and FD&C dye, such as FD&C Red 40, FD&C Yellow 5, FD&C Yellow 6, a D&C dye or a natural colorant such as annatto or other natural colorant which exists in salt form.

In the practice of the invention, a stable, aqueous suspension composition is formulated by combining a water-soluble, nontoxic dye, a metal salt immobilizing agent, with the proportion of metal salt to dye being within the above-described ranges, an opacifying agent which may be either titanium dioxide or iron oxide, and water. This initial suspension composition may be formulated, for example, by adding the nontoxic, water-soluble dye or mixture of dyes and the immobilizing agent to a dispersion of titanium dioxide in water. The quality of the final coating obtained may be further improved by incorporating into the suspension composition fluidizing agent such as ethylene diamine tetraacetic acid, diethylene trimine pentaacetic acid, dehydroxyethyl glycine, nitrilo triacetic acid, hydroxyethylene diamine triacetic acid, iminodiacetic acid or ethanol diglycine.

To prepare the coating suspension for use in film coating tablets and the like, the above-formulated suspension composition is added to an aqueous solution of a film-forming, water-soluble or water-dispersible, edible polymer. Polymers of this type useful in the invention include methyl cellulose, hydroxypropylmethyl cellulose, hydroxypropyl cellulose, polyvinyl pyrrolidone, maltodextrin, polydextrose, modified starches (such as "Purity Gum 59" Marketed by National Starch) and natural gums such as gum tragacanth, gum acacia and xanthan gum. Other conventionally employed polymers and resins of this type may be employed, and mixtures of such polymers may also be used. Hydroxypropylmethyl cellulose is the preferred polymer of this type for use in the practice of the invention. The aqueous solution of such polymer to which the suspension composition is added may also contain a plasticizer such as glycerin, propylene glycol, polyethylene glycol or others known to the art. These components may be stirred together, for example, with a magnetic stirrer (low energy) for a short period of time (e.g. 2 minutes) whereupon the coating suspension is ready for coating tablets and the like.

It should be further noted that since the present invention enables the use of water-soluble dyes, a coating suspension can be directly prepared by incorporating the requisite film-forming, water-soluble or water-dispersible polymer into the above-described suspension composition and thereby produce a coating suspension ready for use in the coating of tablets and the like without additional process steps.

The coating suspension is sprayed onto tablets or the like in conventional manner and produces a smooth, uniform, glossy and non-mottled coating as a result of the nontoxic immobilizing agent immobilizing the water-soluble dye and preventing it from migrating in the coating layer. The practice of the invention not only enables such a desirable coating to be achieved more efficiently and economically, but of equal importance, less color is required to produce the same effect as realized with lakes. Additionally, the elimination of bulky lake pigments from tablet coatings enables the coating suspensions of the present invention to provide more gloss to film coatings and less brittleness to both film and sugar coatings. In this regard, it should be noted that the present invention may be practiced with sugar solutions in which embodiment the initial suspension composition described above is added to a sugar solution containing no film-forming polymer and the resulting coating suspension applied to candy or pharmaceutical dosage forms to produce smooth, uniform, substantially non-mottled coatings.

In another but less preferred embodiment of the invention, the invention can be carried out using a mixture of a nontoxic, water-soluble dye and a lake as the coloring agent, with the lake functioning as a source of aluminum metal salt. When such a mixture is utilized, it has been found that the proportion by weight of lake to dye in the mixture must be in the range of approximately 1:1 to approximately 1:10, with a preferred range being on the order of approximately 1:4. Also, when employing a mixture of dye and lake where the lake constitutes more than 10% by weight of the composition, the suspension composition must also incorporate a fluidizing agent in order to maintain the mixture in a fluid state. Any of the fluidizing agents set forth above may be used for this purpose.

As an additional feature of the invention, dry concentrates of the above-described suspension compositions and coating suspensions may be prepared by dry mixing of the various components. The dry concentrate compositions can then simply be added to the requisite amount of water to form the corresponding suspension compositions or coating suspensions for use in direct coating of tablets and the like in accordance with the invention.

The following examples illustrate the practice of the invention.

EXAMPLE 1

A stable, aqueous suspension was prepared having the following composition:

| Component | Wt. |
| --- | --- |
| FD&C Red 40 dye | 18.0 g. |
| TiO$_2$ | 18.0 g. |
| Calcium chloride | 2.0 g. |
| Water | 62.0 g. |

| Component | Wt. |
|---|---|
| | 100.0 g. |

The dye and calcium chloride immobilizing agent were added to an aqueous dispersion of titanium dioxide with the composition containing 1 equivalent of calcium per mole of dye.

EXAMPLE 2

A coating suspension was prepared having the following composition:

| Component | Wt. |
|---|---|
| Methocel E-5 (10%) | 80.0 g. |
| Polyethylene glycol (PEG-400) | 1.6 g. |
| Suspension of Example 1 | 3.0 g. |
| Water | 15.4 g. |
| | 100.0 g. |

The above ingredients or components were stirred together with a magnetic stirrer and the coating suspension was ready for coating in 2 minutes. The coating suspension was sprayed onto 420 g. of tablets and a bright, smooth, uniform, glossy coating resulted. The coating resulted in a highly desirable, elegant tablet.

EXAMPLE 3

A stable, aqueous suspension was prepared as in Example 1 having the following composition:

| Component | Wt. |
|---|---|
| FD&C Yellow 6 dye | 19.3 g. |
| $TiO_2$ | 19.3 g. |
| Ethylene diamine tetraacetic acid | 0.4 g. |
| Calcium chloride | 1.9 g. |
| Water | 59.1 g. |
| | 100.0 g. |

EXAMPLE 4

A stable, aqueous suspension was prepared as in Example 1 having the following composition:

| Component | Wt. |
|---|---|
| FD&C Yellow 6 dye | 19.5 g. |
| $TiO_2$ | 19.5 g. |
| Ethylene diamine tetraacetic acid | 0.4 g. |
| Magnesium chloride | 1.9 g. |
| Water | 58.7 g. |
| | 100.0 g. |

EXAMPLE 5

A stable, aqueous suspension was prepared as in Example 1 having the following composition:

| Component | Wt. |
|---|---|
| FD&C Yellow 6 dye | 19.3 g. |
| $TiO_2$ | 19.3 g. |
| Ethylene diamine tetraacetic acid | 0.4 g. |
| Calcium carbonate | 1.9 g. |
| Water | 59.1 g. |
| | 100.0 g. |

EXAMPLE 6

A stable, aqueous suspension was prepared as in Example 1 having the following composition:

| Component | Wt. |
|---|---|
| FD&C Yellow 5 dye | 19.4 g. |
| $TiO_2$ | 18.7 g. |
| Ethylene diamine tetraacetic acid | 0.4 g. |
| Magnesium carbonate | 1.9 g. |
| Water | 59.5 g. |

EXAMPLE 7

A stable, aqueous suspension was prepared as in Example 1 having the following composition:

| Component | Wt. |
|---|---|
| FD&C Yellow 5 dye | 18.3 g. |
| $TiO_2$ | 17.0 g. |
| Ethylene diamine tetraacetic acid | 0.4 g. |
| Pharmasorb clay | 4.7 g. |
| Water | 59.5 g. |
| | 100.0 g. |

EXAMPLE 8

A stable, aqueous suspension was prepared as in Example 1 having the following composition:

| Component | Wt. |
|---|---|
| FD&C Red 40 dye | 18.5 g. |
| $TiO_2$ | 17.8 g. |
| Ethylene diamine tetraacetic acid | 0.4 g. |
| Bentonite clay | 3.7 g. |
| Water | 59.6 g. |
| | 100.0 g. |

EXAMPLE 9

A stable, aqueous suspension was prepared as in Example 1 having the following composition:

| Component | Wt. |
|---|---|
| FD&C Red 40 dye | 19.3 g. |
| $TiO_2$ | 18.6 g. |
| Ethylene diamine tetraacetic acid | 0.4 g. |

| Component | Wt. |
|---|---|
| Calcium carbonate | 1.9 g. |
| Water | 59.8 g. |
| | 100.0 g. |

EXAMPLE 10

A stable, aqueous suspension was prepared as in Example 1 having the following composition:

| Component | Wt. |
|---|---|
| FD&C Yellow 5 dye | 19.0 g. |
| TiO$_2$ | 19.0 g. |
| Ethylene diamine tetraacetic acid | 0.4 g. |
| Alumina | 1.9 g. |
| Water | 59.7 g. |
| | 100.0 g. |

EXAMPLE 11

A stable, aqueous suspension was prepared as in Example 1 having the following composition:

| Component | Wt. |
|---|---|
| FD&C Yellow 6 dye | 18.4 g. |
| TiO$_2$ | 18.4 g. |
| Ethylene diamine tetraacetic acid | 0.4 g. |
| Aluminum chloride (28%) | 3.4 g. |
| Water | 59.4 g. |
| | 100.0 g. |

EXAMPLE 12

A stable, aqueous suspension was prepared as in Example 1 having the following composition:

| Component | Wt. |
|---|---|
| FD&C Yellow 5 dye | 19.1 g. |
| TiO$_2$ | 19.1 g. |
| Ethylene diamine tetraacetic acid | 0.4 g. |
| Zinc oxide | 1.9 g. |
| Water | 59.5 g. |
| | 100.0 g. |

EXAMPLE 13

A stable, aqueous suspension was prepared as in Example 1 having the following composition:

| Component | Wt. |
|---|---|
| FD&C Yellow 5 dye | 19.6 g. |
| TiO$_2$ | 19.6 g. |
| Ethylene diamine tetraacetic acid | 0.4 g. |
| Aluminum chloride (28%) | 3.6 g. |
| Water | 59.8 g. |
| | 100.0 g. |

EXAMPLE 14

A stable, aqueous suspension was prepared as in Example 1 having the following composition:

| Component | Wt. |
|---|---|
| FD&C Yellow 5 dye | 19.0 g. |
| TiO$_2$ | 19.0 g. |
| Ethylene diamine tetraacetic acid | 0.4 g. |
| Barium sulfate | 1.9 g. |
| Water | 59.7 g. |
| | 100.0 g. |

EXAMPLE 15

A stable, aqueous suspension was prepared as in Example 1 having the following composition:

| Component | Wt. |
|---|---|
| FD&C Yellow 5 dye | 19.4 g. |
| TiO$_2$ | 19.4 g. |
| Calcuim carbonate | 2.0 g. |
| Water | 60.2 g. |
| | 100.0 g. |

The compositions of Examples 3 through 15 were used as described in Example 2 to produce tablets with a smooth, uniform, substantially non-mottled coating.

EXAMPLE 15

A stable, aqueous suspension was prepared as in Example 1 having the following composition:

| Component | Wt. |
|---|---|
| FD&C Red 40 dye | 15.0 g. |
| FD&C Red 40 dye lake | 15.0 g. |
| TiO$_2$ | 18.0 g. |
| Ethylene diamine tetraacetic acid | 0.5 g. |
| Water | 71.5 g. |
| | 120.0 g. |

In this composition, the incorporation of ethylene diamine tetraacetic acid is essential to keep the composition fluid. Twenty percent more of this composition is required to achieve the same color level as with the composition of Example 1.

EXAMPLE 17

A stable, dry concentrate composition was prepared by mixing the following:

| Component | Wt. |
|---|---|
| FD&C Yellow 5 dye | 46.0 g. |
| TiO$_2$ | 46.0 g. |
| CaCl$_2$.2H$_2$O | 8.0 g. |
| | 100.0 g. |

EXAMPLE 18

A stable, dry concentrate composition was prepared by mixing the following:

| Component | Wt. |
| --- | --- |
| FD&C Red 40 dye | 46.0 g. |
| TiO$_2$ | 46.0 g. |
| Calcium carbonate | 6.5 g. |
| Calcium disodium ethylene diamine tetraacetate | 0.5 g. |
|  | 100.0 g. |

EXAMPLE 19

A stable, aqueous suspension was prepared as in Example 1 having the following composition:

| Component | Wt. |
| --- | --- |
| FD&C Yellow 5 dye | 19.0 g. |
| Cos. Iron oxide Yellow | 1.9 g. |
| TiO$_2$ | 19.0 g. |
| Ethylene diamine tetraacetic acid | 1.1 g. |
| Water | 59.0 g. |
|  | 100.0 g. |

EXAMPLE 20

A stable, aqueous suspension was prepared as in Example 1 having the following composition:

| Component | Wt. |
| --- | --- |
| FD&C Yellow 5 dye | 19.5 g. |
| TiO$_2$ | 19.5 g. |
| Ethylene diamine tetraacetic acid | 1.1 g. |
| Dicalcium phosphate | 1.0 g. |
| Water | 59.9 g. |
|  | 100.0 g. |

The compositions of Examples 19 and 20 when used as described in Example 2 produced tablets with smooth, uniform, non-mottled coatings.

In view of the above, it will be seen that the several objects of the invention are achieved and other advantageous results obtained.

As various changes could be made in the above compositions and methods without departing from the scope of the invention, it is intended that all matter contained in the above description shall be interpreted as illustrative and not in a limiting sense.

What is claimed is:

1. A stable, dry concentrate composition for use in preparing a stable, aqueous suspension composition comprising:
   (i) a water-soluble, nontoxic dye,
   (ii) an opacifying agent selected from the group consisting of titanium dioxide and iron oxide, and
   (iii) a nontoxic immobilizing agent, said nontoxic immobilizing agent being constituted by a nontoxic metal salt present in an amount from approximately 0.1 to approximately 10 equivalents of metal per mole of said dye.

2. A stable, dry concentrate composition as set forth in claim 1 wherein said nontoxic metal salt is present in an amount of from approximately 0.5 to approximately 5 equivalents of metal per mole of said dye.

3. A stable, dry concentrate composition as set forth in claim 1 wherein said nontoxic metal salt is selected from the group consisting of alkaline earth metal salts, iron salts, aluminum salts and zinc salts.

4. A stable, dry concentrate composition as set forth in claim 1 wherein said nontoxic metal salt is selected from the group consisting of calcium and magnesium salts.

5. A stable, dry concentrate composition as set forth in claim 1 wherein said opacifying agent is titanium dioxide.

6. A stable, dry concentrate composition as set forth in claim 1 wherein said water-soluble, nontoxic dye is selected from the group consisting of water-soluble FD&C and D&C dyes.

7. A stable, dry concentrate composition as set forth in claim 1 wherein said composition additionally includes a fluidizing agent selected from the group consisting of ethylene diamine tetraacetic acid, diethylene triamine pentaacetic acid, dihydroxyethyl glycine, nitrilo triacetic acid, hydroxyethylene diamine triacetic acid, iminodiacetic acid and ethanol diglycine.

8. A stable, dry concentrate composition for use in preparing a coating suspension for coating tablets and the like comprising the stable, dry concentrate composition of claim 1 and a film-forming, water-soluble or water-dispersible, edible polymer.

9. A stable, dry concentrate composition as set forth in claim 8 wherein said polymer is selected form the group consisting of methyl cellulose, hydroxypropylmethyl cellulose, hydroxypropyl cellulose, polyvinyl pyrrolidone, maltodextrin, polydextrose, modified starches and a natural gum selected from the group consisting of gum tragacanth, gum acacia and xanthan gum.

10. A stable, dry concentrate composition as set forth in claim 8 wherein said polymer is hydroxypropylmethyl cellulose.

11. A stable, dry concentrate composition as set forth in claim 8 wherein said composition additionally includes a plasticizer.

12. The composition of claim 1 in which the nontoxic immobilizing agent is applied to an object selected from the group consisting of tablets, candy pieces, nuts, seeds, capsules and granules.

\* \* \* \* \*

UNITED STATES PATENT AND TRADEMARK OFFICE
CERTIFICATE OF CORRECTION

PATENT NO. : 5,595,592
DATED : January 21, 1997
INVENTOR(S) : Charles A. Signorino, et al.

It is certified that error appears in the above-indentified patent and that said Letters Patent is hereby corrected as shown below:

Column 1, line 40, delete "table" and replace with -- tablet --;

Column 2, line 41, between water-dispersible and edible insert -- , --;

Column 3, line 21, delete "water-soluble" and replace with -- water-insoluble --;

Column 3, line 44, between composition and fluidizing insert -- a --.

Signed and Sealed this

Twelfth Day of August, 1997

Attest:

BRUCE LEHMAN

Attesting Officer

Commissioner of Patents and Trademarks